United States Patent [19]

Goldstein

[11] Patent Number: 4,609,627
[45] Date of Patent: Sep. 2, 1986

[54] ENZYMATIC CONVERSION OF CERTAIN SUB-TYPE A AND AB ERYTHROCYTES

[75] Inventor: Jack Goldstein, New York, N.Y.

[73] Assignee: New York Blood Center, Inc., New York, N.Y.

[21] Appl. No.: 518,980

[22] Filed: Aug. 1, 1983

[51] Int. Cl.$^4$ .......................... C07K 3/00; A01N 1/02; C12N 9/24; C12N 9/40
[52] U.S. Cl. ......................................... 435/269; 435/2; 435/200; 435/208; 424/88; 424/101
[58] Field of Search ................... 435/269, 2, 200, 208; 424/88, 101

[56] References Cited

U.S. PATENT DOCUMENTS

| | | | |
|---|---|---|---|
| 4,112,070 | 9/1978 | Harmening | 435/2 |
| 4,330,619 | 5/1982 | Goldstein | 435/2 |
| 4,427,777 | 1/1984 | Goldstein | 435/2 |

OTHER PUBLICATIONS

Levy, G. N. et al., Journal of Biol. Chem., vol. 255, (24), 11737–11742 (1980).
Goldstein, J. et al., Science, vol. 215, (4529) (pp. 168–170), Jan. 8, 1982, (Goldstein, III).
Uda, Yutaka et al., The Journal of Biological Chemistry, vol. 252, (15) pp. 5194–5200, (Aug. 10, 1977).

Primary Examiner—Sidney Marantz
Assistant Examiner—L. Krawczewicz
Attorney, Agent, or Firm—Sprung Horn Kramer & Woods

[57] ABSTRACT

Type O erythrocytes are produced from certain sub-types of A erythrocytes or type AB erythrocytes by contacting the same following equilibration of a pH of 5.6–5.8 with an $\alpha$-N-acetylgalactosaminidase, preferably obtained from an avian liver, for periods sufficient to convert the A antigen in the erythrocyte to the H antigen. Following removal of the enzyme, the erythrocyte is re-equilibrated to a pH of 7.2–7.4. As a result, there is obtained O type erythrocytes characterized by a 60 to 90 percent ATP level based on the level of ATP in naturally occurring O or AB erythrocytes. Beginning with certain A cells one obtains synthetic O erythrocytes characterized by a terminal $\alpha$-fucose moiety, O antigenicity, and the absence of A antigenicity. Beginning with $A_2B$ erythrocytes, one obtains B erythrocytes by the same process characterized by the absence of A antigenicity, greater H antigenicity than naturally occurring $A_2B$ cells, the presence of B antigenicity and the aforedescribed ATP levels.

17 Claims, 1 Drawing Figure

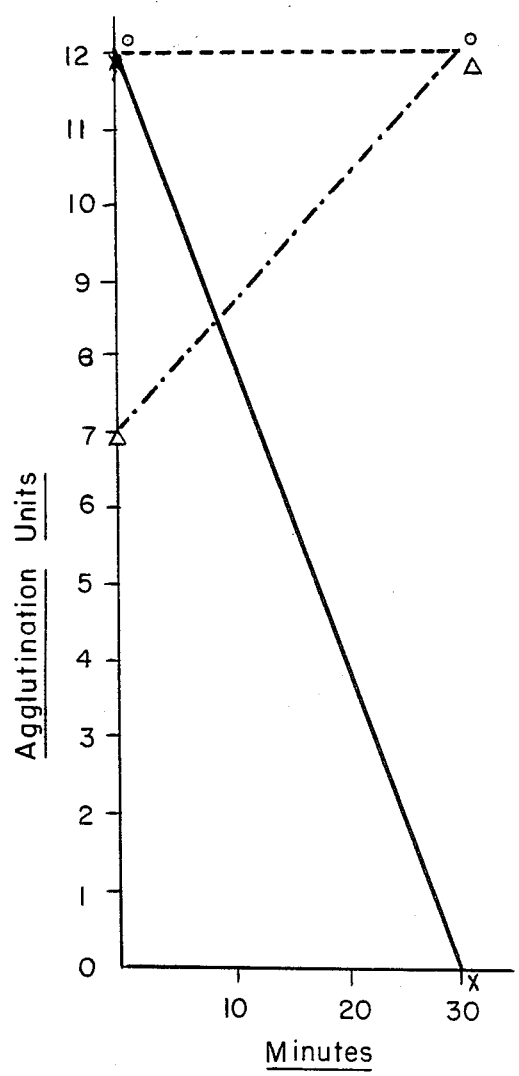

ENZYMATIC CONVERSION OF CERTAIN SUB-TYPE A AND AB ERYTHROCYTES

BACKGROUND OF THE INVENTION

1. Field of the Invention

This invention relates to the conversion of certain sub-types of blood type A erythrocytes into type O cells to render for use in tranfusion therapy. More especially, this invention relates to a process for the conversion of certain sub-type A erythrocytes into type O cells under conditions whereby the cells do not lose their cellular functions, are suitable for the adsorption and release of oxygen whereby the cells can be transfused in the manner of type O blood. This invention also relates to the products obtained by the conversion of such erythrocyte sub-types into type O cells.

2. Discussion of Prior Art p As is well known in the transfusion therapy, it is necessary to match the blood type of the recipient with the type of blood available in the blood bank. Thus, for instance, a recipient of type A blood can only be safely transfused with type A blood. The exception to this is type O blood, the erythrocytes of which can be safely transfused into type A, type B and type A, B recipients as well as O recipients.

In the operation of a blood bank or other facility which accumulates whole blood or at least the red cell component thereof, it is necessary to maintain supplies of each type of blood. It has not heretofore been possible to maintain only O type blood because there is a paucity of O type donors. O type donor blood has therefore been used largely for O type recipients. On the other hand, a majority of donors have A, B or AB blood and there can exist from time to time, an excess of these types of blood. It has become desirable, therefore, to adjust the supply to the demand. Specifically, it has been desired to convert A, B or AB type blood to an O type blood type—a universal donor.

The ABO blood group system was the first to be discovered and is the one of greatest importance from the point of view of blood transfusion. Individuals of blood types A, B and O express A, B and H antigens respectively. These antigens are not only found in the red cells, but on the surfaces of all endothelial and most epithelial cells as well. In addition, glycoproteins having A, B and H antigenicity are also found in the tissue fluids and secretions of those individuals who have the ability, inherited as a Mendelian dominant character, to secrete these blood group substances, or factors as they are termed.

While the blood group substances are glycoproteins, the A B H active material obtained from the cell membranes appear to be glycolipids and glycoproteins.

Considerable work has been done to determine the structures of the A B H determinants. It was found that the blood group specificity of the entire molecule, which may contain one or more carbohydrate chains, attached to a peptide backbone, is determined by the nature and linkage of those monosaccharides situated at the non-reducing ends of these chains. The most important sugar for each specificity, often referred to as the immuno-dominant or immuno-determinant sugar, was found to be as follows: for H antigen, fucose; for A antigen, N-acetyl-galactosamine; and for the type B antigen, galactose. More recently, studies with A B H active glycolipids obtained from erythrocyte cell membranes also show the presence of the same immunodominant sugars at the reducing ends of the carbohydrate chains, attached to adjacent sugars by the same linkages. The carbohydrate chains are, in turn, linked either to protein or the ceramide, which is embedded in the lipid bi-layer of the membrane. The length of the carbohydrate moiety may vary and it may have either a straight or branched structure. Thus far, four variants of blood group active A glycolipid, two of B and three of H, have been isolated from the erythrocyte cell membrane.

Through these studies, it was theorized that one could convert a type A or type B antigen into a type H antigen, corresponding to a type O cell by removal of one of the monosaccharide groups pendent from the cell.

It has recently been demonstrated that the galactose molecule responsible for B antigenicity can be enzymatically removed from type B cells, thus converting them to type O erythrocytes under conditions that maintain cell viability and membrane integrity. Furthermore, it has been shown that one ml quantities of such enzymatically coverted cells survive not only normally in the circulation when returned to the original type B donor, but also when such quantities are transfused to A and O recipients whose immune systems would not tolerate unconverted type B cells (Goldstein, J., Siviglia, G., Hurst, R., Lenny L. and Reich L., Science 215 168, 1982). See also U.S. Pat. No. 4,330,619 disclosing conversion of B erythrocytes to O erythrocytes using $\alpha$-galactosidase.

Specifically, in the case of A antigen it was also postulated that the N-acetylgalactosamine moiety of the type A-antigen could be removed enzymatically whereby the type A antigen would be converted to type H antigen. A previous attempt has been made to accomplish such an enzymatic conversion and produce transfusable quality cells. See Levy and Animoff, Journal of Biological Chemistry Vol. 255, No. 24, Dec. 25, 1980, pages 11737–42. This was unsuccessful, however, because only a partial removal of A antigenicity was achieved by the bacterial enzyme employed since these treated cells were still agglutinated (up to sixteen fold dilution) with human anti A antiserum. Such cells are not viable for transfusion to type O and B recipients becasue they would produce the same effect as untreated type A erythrocytes, inducing transfusion reactions and being destroyed by the recipient's immune system. Furthermore, this bacterial enzyme is contaminated with significant amounts (0.1%) of another enzyme known as sialidase. Treatment of erythrocytes with sialidase results in their premature aging, i.e. the uncovering of cryptic antigens resulting in agglutination of these cells by all human sera which leads to their rapid removal from the circulation following transfusion. Thus, even if all A antigenicity had been removed, the sialidase present in the bacterial enzyme preparation renders such treated cells unfit for transfusion.

There are three recognized major subtypes of blood type A known as $A_1$, A intermediate or $A_{int}$ and $A_2$. There are both quantitative and qualitative differences distinguishing the subtypes. $A_1$ cells have more antigenic A sites, i.e. terminal N-acetylgalactosamine residues, than $A_{int}$ cells which in turn have more than $A_2$ erythrocytes. Qualitatively the transferase enzymes responsible for the formation of A antigens differ biochemically from each other in $A_1$, $A_{int}$ and $A_2$ individuals. This suggests a genetic basis for three subtypes, namely that the A genetic locus is subdivided into three common genetic sites, each representing a different subtype and each site coding for its own specific transferase enzyme.

The number of $A_{int}$ and $A_2$ individuals vary widely in different populations. For example, the frequency of $A_2$ is approximately 30% of $A_1$ in Caucasians (British) and less than 1% in Orientals (Japanese). Whereas the frequency of $A_{int}$ is only about 1–2.5% of A in Caucasians, 0.5% in Orientals but ranges from 1–32% in blacks.

It is an object of this invention, therefore, to provide a process in which the terminal moiety of the A-antigenic determinant of stroma from certain sub-type, of A and AB type cells can be removed while leaving the red cells intact so that the resultant composition can be used in transfusion therapy. Specifically, it is an object of this invention to convert sub-types A and AB cells to O type cells whereby the cells remain intact and undergo little if any hemolysis and the resultant composition can be used in transfusion therapy. Specifically, it is an object of this invention to covert certain sub-types of A and AB cells to O type cells whereby the cells remain intact and undergo little if any hemolysis and the resultant composition can be used in transfusion therapy. The invention is directed to the conversion of A (intermediate) and $A_2$ cells and the corresponding A B cells into O cells. These cells which are converted into O cells are hereinafter designated as "$A_{int}$–$A_2$ cells", it being understood that the term embraces corresponding B cells, e.g. $A_2$ B cells.

SUMMARY OF THE INVENTION p The foregoing objects are attained, in accordance with this invention, by a process which comprises:

A. equilibrating said $A_{int}$–$A_2$ erythrocytes to a pH of 5.6–5.8.
B. thereafter, contacting the so-equilibrated erythrocytes with an enzyme for a period sufficient to convert said cells to cells having H-antigenicity.
C. removing said enzyme from said erythrocytes; and
D. re-equilibrating said erythrocytes to a pH of 7.2–7.4.

The process is preferably conducted using an α N-acetyl galactosaminidase obtained from avian liver. Various avian livers can be used including those of chickens, turkeys, pigeons, etc. It has been found that α-N-Acetylgalactosaminidase obtained from such source has superior activity in respect of the enzymatic conversion. Such enzyme source is further preferred because the active component can be separated from other liver proteins so that the reactive mass is purer than N-acetylgalactosaminidases obtained from other sources such as from bacteria and the liver of mammals. As a result, better cleavage of the N-acetylgalactosamine moiety is achieved with the result that a pure and more biologically compatible product is obtained. Converted cells fo the invention perform in the manner of naturally occurring O type erythrocytes and can be used in transfusion therapy.

Depending upon the antigenicity of the starting erythrocyte, different products are obtained. Thus, when starting with $A_2$ B erythrocytes, a type B erythrocyte is produced characterized by:

A. the absence of A antigenicity;
B. a greater H antigenicity than naturally occurring $A_2$ B cells;
C. the presence of B antigenicity;
D. 60 to 90% of the adenosene-5'-triphosphate (ATP) content of naturally occurring $A_2$ B erythrocytes.

Such converted $A_2$ B erthrocytes can further be characterized by a 2,3-diphosphoglyceric acid (2,3 DPG) level of 60 to 90% of naturally occurring $A_2$ B erythrocytes. Generally, such converted $A_2$ B erythrocytes (now B erythrocytes) have a met-hemoglobin level of 2–6% of total hemoglobin in the erythrocytes compared with a met-hemoglobin level of naturally occurring $A_2$ B cells in the range of 0.1–1%, based on the weight of total cell hemoglobin. Preferably, each of the ATP and 2,3-DPG levels are in the range of 70–90% and especially 80–90%.

When the enzymatic conversion is performed on $A_{int}$–$A_2$ cells which are not also in the B form, the product is a type O erythrocyte further characterized by:

A. a terminal α-fucose moiety
B. O antigenicity
C. the absence of A antigenicity
D. 60 to 90% of the adenosene-5'-triphosphage (ATP) content of naturally occurring O erythrocytes.

As in the case of type B erythrocytes derived from $A_2$ B erythrocytes, the 2,3-DPG level is usually 60 to 90% of that of naturally occurring B erythrocytes. Similarly, it is preferred that the ATP and 2,3-DPG levels be in the range of 70 to 90% and especially 80 to 90% of that of naturally occurring erythrocytes. These levels can be expressed either on a weight or volume basis and the levels are generally measured by biochemical procedures. These are set forth in Sigma Technical Bulletin No. 366-UV for ATP and Sigma Technical Bulletin No. 35-UV for 2,3 DPG.

The B erythrocytes derived from $A_2$ B erythrocytes preferably have at least 20% greater H antigenicity than naturally occurring $A_2$ B cells. The H antigenicity can be measured by a lectin obtained from the seeds of the plant Urex europaeus.

The converted $A_2$ B erythrocytes are characterized by B antigenicity. This B antigenicity is determined by reaction with human anti-B antiserum. Similarly, the O erythrocytes derived from $A_{int}$–$A_2$ erythrocytes can be characterized by at least 2 million terminal α-fucose moieties. The absence of A antigenicity is revealed by the absence of reaction with human anti-A antiserum.

The O cells which are recovered as a result of this process are substantially free of terminally α-linked N-acetylgalactosamine moiety which was present on the original $A_{int}$–$A_2$ cells.

If $A_2$ B cells are converted to B cells, these in turn can be converted into O cells by the method of U.S. Pat. No. 4,330,619.

In the procedure of the invention, α-N-acetylgalactosaminidase is employed as the enzyme. The same can be in a free enzymatic form or can be disposed on a support. The support can either be a soluble support such as dextran or polyethyleneglycol or can be an insoluble support such as cellulose, and cross linked polymers of acrylamide, dextran and agarose.

The realization of non-hemolyzed erythrocytes in the H-antigen type is effected by initial equilibration of the $A_{int}$–$A_2$ erythrocytes in the absence of enzyme to a critical pH of 5.6 to 5.8. The equilibration is desirably effected using a citrate-phosphate buffer of pH 5.6 to 5.8 which contains citric acid in a concentration of 0.02–0.05M in addition to dibasic sodium phosphate in a concentration of 0.05 to 0.10M and sodium chloride in a concentration of 0.15M.

The equilibration is normally effected by suspending the erythrocytes in the buffer solution for a period of at least 5 minutes, preferably no longer than 15 minutes. In accordance with the preferred mode of this invention, the buffer is removed from the erythrocytes and fresh buffer is added again allowing the contact to be for a period of at least 5 minutes and preferably no longer than 15 minutes. Desirably, a third contact of the erythrocytes with another fresh aliquot or buffer is effected, this third contact also being for at least 5 minutes, and preferably no longer than 15 minutes.

While in vitro tests reflect that the total contact time of the buffer with the erythrocytes can be up to two hours, it is preferred for in vivo considerations that the contact time not exceed two hours, preferably no shorter than ½ hour and preferably no longer than one hour. It must be remembered that the objective is to convert the A antigen to the H antigen while leaving the cellular body intact so that when employed in transfusion therapy, the cells can perform their normal fuctions, especially the adsorption and release of oxygen.

It is another extremely important feature of the invention that the contact of the erythrocytes with the enzyme occur only after the cells have been equilibrated to 5.6–5.8. In other words, the erythrocytes are not initially contacted with enzyme while in admixture with a pH lowering substance (buffer).

The equilibration to 5.6–5.8 is effected at 20°–26° C. preferably at room temperature. Sub-atmospheric and super-atmospheric pressures are not required, atmospheric pressure being employed.

Once the erythrocytes have been equilibrated to 5.6–5.8, the enzymatic conversion of the A type antigen to the H type antigen becomes simplified. The enzymatic reaction is effected by the use of $\alpha$-N-acetylgalactosaminidase in the free or supported form employing 12–250 enzyme units per 100–1,000 $\mu$l of cells. Preferably, the enzyme is present in an amount of 160–200 units per 800–1,000 $\mu$l of cells.

The enzymatic conversion is effected at 26°–37° C. preferably 32°–37° C. for 30–150 minutes, preferably 45–60 minutes.

As indicated above, the enzyme can be in the form of a free enzyme or in the form of a supported enzyme, the support being either a soluble or insoluble support. Dextran is a preferred soluble support, especially dextran of weight average in molecular weight 20,000 to 80,000. Another desirable soluble support is polyethyleneglycol of weight average in molecular weight 10,000 to 80,000. Solid (insoluble) supports include cross-linked dextrans, agarose and cellulose.

Following the enzyme treatment, the enzyme is removed from the erythrocytes and erythrocytes are re-equilibrated to pH 7.2 to 7.4 by washing the same with a buffer and allowing to remain in contact with the buffer from 15–30 minutes following the last wash. The washing is for the dual purpose of adjusting the pH to 7.2–7.4 and removing enzyme and free N-acetylgalactosamindase. Washing solutions which can be employed include those containing the following buffer: phosphate buffered saline which contains a concentration of 0.01M potassium phosphate in the ratio of seven parts dibasic salt to three parts monobasic and a concentration of 0.9% sodium chloride. The washing is effected for at least three times, preferably three to five times at a temperature of 20° to 26° C., preferably room temperature. There is no required time of washing except that the washing should be performed until one can no longer detect the presence of enzyme in the wash solution.

Thereafter, the cells are in the H-antigen form and can be used for transfusion therapy. For purposes of use in transfusion, the cells are diluted with a physiologically acceptable medium. Physiologically acceptable mediums include sterile isotonic saline solution consisting of 0.9% sodium chloride and sterile isotonic solution containing 0.2% dextrose. Generally speaking, the concentration of the cells in the medium is between 40% and 70%, preferably between 40% and 45%. These conditions are comparable to those used for transfusion of fresh and frozen-thawed packed erythrocytes. The cells of the invention can be transfused in the same manner as known packed cells are transfused.

Cellular metabolic studies indicate that Adenosine-5'-triphosphates (ATP) content remain above 60% and 2,3-diphosphoglyceric acid (2,3 DPG) levels above 60% also remain after treatment. This allows for maintenance of cell shape and for normal oxygen-binding and exchange.

The buffer and incubation conditions employed in accordance with the method provide a product at which there is an 80–90% or more retention of ATP levels and 70–90% of, 2,3 DPG for up to 3 hours of incubation.

By using $\alpha$-N-acetylgalactosaminidase as the enzyme, there was obtained a complete conversion of $A_{int}$–$A_2$ cells to H activity. The time needed for this conversion is enzyme dependent and can be reduced by increasing amounts of enzyme. Microsposcopic examination of these cells reveals them to be free of gross morphological abnormalities and to be capable of spherocyte discocyte interconversion. 3-membrane components, the Rh and M and N antigens and sialic acid, show no gross changes between the original A cells and the converted H cells. Also, when type $A_2B$ cells are converted to BH with this enzyme, there is no change in the levels of B activity of the cells and B and O (H) cells have been found to have their activities unaffected by the enzyme. Converted cells were checked with autologous plasma and do not shown any panagglutination.

It is desired that the conversion be effected when the enzyme is employed in the form of a supported enzyme. Preferably, the support is a soluble support and most preferably it is a dextran of the molecular weight 20,000 to 80,000. The enzyme can be attached to the soluble support using cyanogen bromide as a covalent linking agent. However, in order to separate the enzyme dextran conjugate from unbound material, it may be necessary to subject the crude enzyme preparation to a simple purification procedure using Spehadex G-100 gel filtration prior to binding dextran. Purification conditions permit the use of a product of covalently bound enzyme on dextran or other soluble support which is completely free of unbound material. The enzyme-soluble support conjugate e.g. enzyme dextran conjugate has the same specificity and ability for removal of the A determinant from the surface of the red cells as the free enzyme preparation and can be reused and stored without loss of activity. The use of such a conjugate is desired since they can be used repeatedly and their use is not characterized by side reactions due to impurities in starting enzyme material as is the case when free enzyme is employed. These impurities can be more readily controlled making it possible to use only partially purified preparations for coupling.

Immobolized enzymes can be more readily separated from their substrates to minimize the possibility that some of the glycosidase molecules or contaminating proteins of free enzyme preparations will bind irreversibly to the cell structure, thus introducing potential antibody-producing substances or be removable only under stringent washing conditions likely to damage the membrane of the cell.

Fresh chicken livers are trimmed of extraneous fat and dehydrated either by extraction with acetone or by freeze drying. The dried and powdered chicken liver (140 gm) is mixed with 0.01M sodium acetate pH 4.0 at 4° C. and blenderized (10–30") in order to insure a fine suspension which is allowed to settle (2–16 hr). Recovery of the supernatant is effected by centrifugation. Solid ammonium sulfate is then slowly added to the supernatant to a concentration of 30%. The resulting precipitate is centrifuged away and ammonium sulfate is again added to a final concentration of 50% yielding a precipitate containing as part of a mixture of other enzymes and proteins the enzyme to be used, $\alpha$-N-acetylgalactosaminidase. The precipitate is pelleted by centrifugation, dialyzed against 0.01M sodium acetate pH 5.0 to remove adhering ammonium sulfate and allow the pellet to dissolve. Contaminating substances are then separated from the $\alpha$-N-acetylgalactosaminidase by subjecting the solubilized mixture first to ion exchange chromatography and then gel friction filtration. Specifically, a volume of the mixture containing 1500–1800 units of $\alpha$-N-acetylgalactosaminidase is applied to a column (5×16 cm, 300 ml) of the cation exchanger, carboxymethylcellulose (CM-52 Whatman) equilibrated in 0.01M sodium acetate pH 5.0. Following washing of the column with 0.05M sodium acetate pH 5.0, a linear gradient ranging from 0.07M sodium acetate to 0.20M sodium acetate pH 5.0 is applied (750 ml of each) which results in the elution of a protein fraction containing $\alpha$-N-acetylgalactosaminidase. This fraction is then dialyzed against 0.01M potassium phosphate buffer pH 6.0 and applied to a column (2.5×13 cm, 60 ml) containing the anion exchanger diethylaminoethyl sephadex (A-50 Pharmacia) equilibrated with the same buffer. The column is then washed with this same buffer resulting in the elution of an $\alpha$-acetylgalactosaminidase containing-fraction which is concentrated and subjected to gel filtration through a column (2.5×10 cm) containing porous agarose (Sephadex G-100 Pharmacia). The elution region containing the enzyme is concentrated and subjected once more to gel filtration, this time using a porous polyacrylamide-agarose mixture containing column (BioGel P-150, Bio Rad; 2.5×150). The enzyme fraction thus obtained can be used for the conversion of $A_{int}$–$A_2$ cells to H antigenicity as described here.

No detectable exoglycosidase activities are found except for $\alpha$-galactosidase which is present at 7.6% of the activity of $\alpha$-N-acetylgalactosaminidase at pH 5.7 and 32°. The enzyme activity is 24–30 units/mg protein at pH 4 and 37° C. or 3–4 units/mg protein at pH 5.7 and 32° C. Its isoelectric point at 4° C. is between 7.5 and 7.8 as determined by electrofocusing. Preparation of enzyme from avian livers are known (Wong and Weissman, Biochemistry, Vol. 16, No. 6, 1971, pages 1067–1072), although such known methods have not provided the desired enzyme at such activity levels or at such freedom for exoglycosidase.

The A-intermediate-A2 and A2B cells are distinguished from A1 cells by using anti-A1 lectin in the slide procedure as described by Acugenics in their flyer 1-DL-C-01 issued August 1981. According to this procedure types A1 and A1B strongly agglutinate within one minute. A intermediate cells will weakly agglutinate and A2 and A2B cells show no agglutination during this time period.

EXAMPLE AND DRAWING

In order to more fully illustrate the nature of the invention and the manner of practicing the same, the following example is presented. The annexed figure plots conversion of $A_2B$ cells to HB cells in terms of agglutination units as a function of time, showing that the A antigenicity is completely converted to H antigenicity ("O" cells), that the B antigenicity remains constant and H antigens increase to the level of O cells.

EXAMPLE

Using the enzyme prepared as set forth above, complete conversion of $A_{int}$–$A_2$ cells to H activity and $A_2B$ cells to their respective HB counterparts are measured by a hemagglutination assay. The time needed for this conversion is again enzymatically dependent and can be reduced by increasing amounts of enzymes as, for example, in the case of $A_{int}$ cells (0.1 ml) from 90 minutes (7 units) to 60 minutes (12 units) to 30 minutes (18 units). The results of this typical enzymatic treatment of cells is shown in Table 1. The treatment conditions included citrate-phosphate buffer pH 5.7 (0.02M citric acid and 0.06M dibasic sodium phosphate) in isotonic saline incubation at 32° C. and the use of a rotary mixer at slow speed.

TABLE 1

RATE OF LOSS OF A ANTIGENIC ACTIVITY FROM ENZYME-TREATED HUMAN RED CELLS*

| 100 ul Group A *Erthrocytes incubated with | Anti A Hemagglutination Score at: | | | | |
|---|---|---|---|---|---|
| | 30' | 60' | 90' | 120' | 180' |
| 7 units $\alpha$-N—acetylgalactosaminidase | — | 5 | 4 | 0 | — |
| 12 units $\alpha$-N—acetylgalactosaminidase | 5 | 3 | 0 | — | — |
| 18 units $\alpha$-N—acetylgalactosaminidase | 0 | — | — | — | — |

What is claimed is:

1. A composition comprising type B erythrocytes, said erythrocytes characterized by
   (a) the absence of A antigenicity,
   (b) greater H antigenicity than naturally occurring $A_2B$ cells,
   (c) presence of B antigenicity and
   (d) 60–90% of the adenosine-5'-triphosphate (ATP) content of naturally occurring $A_2B$ erythrocytes, said composition produced by
   (i) equilibrating $A_2B$ erythrocytes to a pH of 5.6 to 5.8;
   (ii) thereafter contacting the so-equilibrated erythrocytes with an alpha-N-acetylgalactosaminidase enzyme for a period sufficient to convert the A antigen in said erythrocyte to the H-antigen;
   (iii) removing said enzyme from said erythrocytes; and
   (iv) re-equilibrating said erythrocytes to a pH of 7.2 to 7.4.

2. A composition according to claim 1, wherein said erythrocytes have a 2,3-diphosphoglyceric acid (2,3-DPG) level of 60–90% of naturally occurring $A_2B$ erythrocytes.

3. A composition according to claim 2, wherein said erythrocytes have a met-hemoglobin level of 2–6% of total hemoglobin in the erythrocytes.

4. A composition according to claim 3, wherein said erythrocytes have 70–90% of the ATP content of naturally occurring $A_2B$ erythrocytes.

5. A composition according to claim 3, wherein said erythrocytes have 80–90% of the ATP content of naturally occurring $A_2B$ erythrocytes.

6. A composition according to claim 1, wherein said B erythrocytes have at least 20% greater H antigenicity than naturally occurring $A_2B$ cells.

7. A composition comprising type B erythrocytes, said erythrocytes characterized by
   (a) the absence of A antigenicity,
   (b) at least 20% greater H antigenicity than naturally occurring $A_2B$ cells,
   (c) presence of B antigenicity,
   (d) 70 to 90% of the adenosine-5′-triphosphate (ATP) content of naturally occurring $A_2B$ erythrocytes,
   (e) 80 to 90% of the 2,3-diphosphoglyceric acid (2,3 DPG) level of naturally occurring $A_2B$ erythrocytes, and
   (f) a met-hemoglobin level of 2–6% of total hemoglobin in the erythrocytes, said composition produced by
   (i) equilibrating $A_2B$ erythrocytes to a pH of 5.6 to 5.8;
   (ii) thereafter contacting the so-equilibrated erythrocytes with an alpha-N-acetylgalactosaminidase enzyme for a period sufficient to convert the A antigen in said erythrocyte to the H-antigen;
   (iii) removing said enzyme from said erythrocytes; and
   (iv) re-equilibrating said erythrocytes to a pH of 7.2 to 7.4.

8. A process for converting $A_{int}$–$A_2$ including $A_2B$ erythrocytes to erythrocytes of the H antigen type which comprises:
   (a) equilibrating said erythrocytes to a pH of 5.6–5.8;
   (b) thereafter contacting the so-equilibrated erythrocytes with an $\alpha$-N-acetylgalactosaminidase enzyme for a period sufficient to convert the A antigen in said erythrocyte to the H-antigen;
   (c) removing said enzyme from said erythrocytes; and
   (d) re-equilibrating said erythrocytes to a pH of 7.2–7.4.

9. A process according to claim 8, wherein said N-acetylglactosaminidase is one obtained from an avian liver.

10. A process according to claim 9, wherein said N-acetylgalactosaminidase has 3–4 enzyme units per ml of protein at pH 5.7 and 32° C.

11. A process according to claim 9, wherein said enzyme is in the free enzyme form.

12. A process according to claim 9, wherein $A_{int}$–$A_2$ cells which are not in the B form are converted to the H antigen form.

13. A process according to claim 9, wherein said $\alpha$-N-acetylgalactosaminidase has an enzyme activity of 24–30 units per ml at pH of 4 and at 37° C.

14. A process according to claim 3, wherein said enzyme has an isoelectric point at 4° C. of between 7.5 and 7.8.

15. A process according to claim 9, wherein said enzyme is in a supported form. pg,35

16. A process according to claim 15, wherein said support is a soluble support.

17. A process according to claim 15, wherein said support is an insoluble support.

* * * * *